(12) United States Patent
Kim et al.

(10) Patent No.: US 10,898,120 B2
(45) Date of Patent: *Jan. 26, 2021

(54) USER STATE MONITORING METHOD AND SYSTEM PERFORMING THE SAME

(71) Applicant: KOREA ELECTRONICS TECHNOLOGY INSTITUTE, Seongnam-si (KR)

(72) Inventors: Kunnyun Kim, Yongin-si (KR); Kwang Bum Park, Yongin-si (KR); Won Hyo Kim, Yongin-si (KR); Yeon Hwa Kwak, Seoul (KR)

(73) Assignee: KOREA ELECTRONICS TECHNOLOGY INSTITUTE, Seongnam-si (KR)

( * ) Notice: Subject to any disclaimer, the term of this patent is extended or adjusted under 35 U.S.C. 154(b) by 160 days.

This patent is subject to a terminal disclaimer.

(21) Appl. No.: 15/954,125

(22) Filed: Apr. 16, 2018

(65) Prior Publication Data
US 2018/0228420 A1   Aug. 16, 2018

Related U.S. Application Data

(63) Continuation of application No. PCT/KR2016/001250, filed on Feb. 4, 2016.

(30) Foreign Application Priority Data

Oct. 14, 2015   (KR) ........................ 10-2015-0143354

(51) Int. Cl.
*A61B 5/18*   (2006.01)
*G01L 1/18*   (2006.01)
(Continued)

(52) U.S. Cl.
CPC ................ *A61B 5/18* (2013.01); *A61B 5/024* (2013.01); *A61B 5/0816* (2013.01);
(Continued)

(58) Field of Classification Search
None
See application file for complete search history.

(56) References Cited

U.S. PATENT DOCUMENTS

| 10,219,749 B2* | 3/2019 | Kim .................... G01L 1/2287 |
| 2004/0056520 A1* | 3/2004 | Cho ...................... A47C 7/405 |
| | | 297/218.1 |

(Continued)

FOREIGN PATENT DOCUMENTS

| KR | 20-1999-0025330 A | 7/1999 |
| KR | 10-2011-0089646 A | 8/2011 |

(Continued)

OTHER PUBLICATIONS

International Search Report dated Jun. 27, 2016 of PCT/KR2016/001250 which is the parent application—2 pages.

*Primary Examiner* — Michael R Bloch
(74) *Attorney, Agent, or Firm* — Knobbe Martens Olson & Bear LLP

(57) ABSTRACT

Provided is a system for monitoring a state of a user. The system includes a chair including a backrest and a seat plate, at least one flexible tactile sensor positioned in the back plate or seat plate and configured to sense a motion of a user who sits on the chair. The system further includes a monitoring apparatus configured to monitor the state of the user based on the sensed value received from at least one flexible tactile sensor.

9 Claims, 9 Drawing Sheets

(51) Int. Cl.
*G01L 1/22* (2006.01)
*A61B 5/024* (2006.01)
*A61B 5/08* (2006.01)
*A61B 5/00* (2006.01)
*A61B 5/04* (2006.01)
*G16H 20/30* (2018.01)
*A61B 5/11* (2006.01)

(52) U.S. Cl.
CPC .............. *A61B 5/6893* (2013.01); *G01L 1/18* (2013.01); *G01L 1/2287* (2013.01); *A61B 5/002* (2013.01); *A61B 5/04* (2013.01); *A61B 5/1116* (2013.01); *A61B 5/4809* (2013.01); *A61B 5/6891* (2013.01); *G16H 20/30* (2018.01)

(56) References Cited

U.S. PATENT DOCUMENTS

| | | | |
|---|---|---|---|
| 2008/0071177 A1* | 3/2008 | Yanagidaira | A61B 5/024 600/483 |
| 2012/0078123 A1 | 3/2012 | Futatsuyama et al. | |
| 2012/0116251 A1* | 5/2012 | Ben-Shalom | A61B 5/11 600/587 |
| 2012/0212353 A1 | 8/2012 | Fung et al. | |
| 2013/0070043 A1 | 3/2013 | Geva et al. | |
| 2013/0072767 A1* | 3/2013 | Imamura | A61B 5/024 600/301 |
| 2014/0039330 A1 | 2/2014 | Seo et al. | |
| 2015/0352990 A1* | 12/2015 | Zouzal | A47C 4/54 297/284.3 |

FOREIGN PATENT DOCUMENTS

| | | |
|---|---|---|
| KR | 10-2013-0029641 A | 3/2013 |
| KR | 10-2014-0003820 A | 1/2014 |
| KR | 10-2014-0011092 A | 1/2014 |
| KR | 10-2014-0032082 A | 3/2014 |
| KR | 10-2014-0074567 A | 6/2014 |
| WO | WO-2011096144 A1 * 8/2011 ........... A61B 5/0816 |
| WO | 2013/109154 A1 | 7/2013 |
| WO | 2015/127193 A1 | 8/2015 |

* cited by examiner

USER STATE MONITORING METHOD AND SYSTEM PERFORMING THE SAME

CROSS-REFERENCE TO RELATED APPLICATIONS

This application is a continuation application, and claims the benefit under 35 U.S.C. §§ 120 and 365 of PCT Application No. PCT/KR2016/001250, filed on Feb. 4, 2016, which is hereby incorporated by reference. PCT/KR2016/001250 also claimed priority from Korean Patent Application No. 10-2015-0143354 filed on Oct. 14, 2015, which is hereby incorporated by reference.

BACKGROUND

Field

The present disclosure relates to monitoring a state of a driver in a vehicle using a flexible tactile sensor.

Related Art

In recent years, healthcare technology is combined with sensor technology to collect biometric information of a user and provide information analyzed based on the collected biometric information to the user. For example, the healthcare technology using a chair acquires the biometric information from the chair which the user uses in daily life or work and analyzes the acquired biometric information to provide the information to the user.

Korean Patent Unexamined Publication No. 10-2014-0003820 relates to a user interface method based on the biometric information acquired from the chair and provides a function to output music or voice in a response set according to a health state, stress, or an emotional state of the user through a user terminal such as a personal computer or a smart phone which receives the biometric information acquired through a bio signal sensor to an armrest, a backrest, and a seat plate in order to acquire the biometric information in the chair or output guide voice to induce exercise or breathing.

Korean Patent Unexamined Publication No. 10-2011-0089646 relates to a functional chair which includes a seat supporting a hip portion of a seated person and the backrest supporting a back of the seated person in connection with the seat and having a second sensor for measuring a distance in order to determine the posture of the seated person installed therein. The corresponding technology includes a sensor for measuring a weight of the seated person and a distance sensor to induce the seated person to sit in a correct posture.

National R&D Project: High-tech Convergence Content
  Technology Development Project Task No.: 2017-0-00595
Research Task Title: Development of a motion game and
  bracelet type wearable device recognizing hand gesture
  with offering SDK for AR/VR
Supported Central Government Agencies: Ministry of Science and Technology (Ministry of Information and Communication)

The disclosure of this section is to provide background of the described technology. Applicant notes that this section may contain information available before this application. However, by providing this section, Applicant does not admit that any information contained in this section constitutes prior art.

SUMMARY

The present disclosure is made in association with a Korean national research and development project (research project name: Development of a motion game and bracelet type wearable device recognizing hand gesture with offering SDK for AR/VR, project identification number: 2017-0-00595)

The present disclosure provides a user state monitoring method which can monitor a state of a user who sits on a chair through a flexible tactile sensor that can sense force on both planes and a system performing the same.

The present disclosure provides a user state monitoring method which can naturally monitor respiration or heartbeat of the user who sits on the chair by using the flexible tactile sensor and a system performing the same.

The present disclosure provides a user state monitoring method which can sense whether the user who sits on the chair dozes by using the flexible tactile sensor and call attention of the user and a system performing the same.

The present disclosure provides a user state monitoring method which can correct a seating posture of the user by using the flexible tactile sensor and a system performing the same.

In an aspect, a system for monitoring a state of a user includes: a chair comprising a back plate and a seat plate; at least one flexible tactile sensor positioned in the back plate or seat plate and sensing a motion of a user who sits on the chair and transmitting a sensed value depending on the corresponding motion to the outside; and a monitoring apparatus monitoring the state of the user based on the sensed value received from at least one flexible tactile sensor.

In an embodiment, the monitoring apparatus measures respiration or heartbeat of the user based on the sensed value received from the flexible tactile sensor at a location corresponding to a specific portion of the user.

In an embodiment, the flexible tactile sensor corresponds to a flexible tactile sensor at a location corresponding to a femoral artery of the user.

In an embodiment, the monitoring apparatus calculates an amount or a distribution of force applied to at least one flexible tactile sensor based on the sensed value and monitor whether the user dozes or a seating posture of the user based on a pattern of the calculated amount or distribution of the force.

In an embodiment, the monitoring apparatus monitors whether the user dozes or the posture of the user by compensating the sensed value based on an impact value measured by an impact sensor of a vehicle.

In an embodiment, when it is determined that the user dozes, the monitoring apparatus transmits a control signal for controlling an operation of a peripheral device to call attention of the user.

In an embodiment, the monitoring apparatus compares the posture of the user and a predetermined posture based on the pattern of the calculated amount or distribution of the force and transmits a control signal for adjusting a location or an angle of the chair to allow a chair adjusting apparatus to adjust the location or angle of the chair.

The monitoring apparatus may not transmit the control signal when the impact value measured by the impact sensor of the vehicle is equal to or more than a predetermined value.

In another aspect, a method for monitoring a state of a user includes: receiving a sensed value from at least one flexible tactile sensor positioned in a backrest or a seat plate of a chair; calculating an amount or a distribution of force applied to at least one flexible tactile sensor based on the received sensed value; and monitoring whether the user dozes or a posture of the user based on a pattern of the calculated amount or distribution of the force.

A method and a system for monitoring a movement of a user according to an embodiment of the present disclosure can monitor a state of a user who sits on a chair through a flexible tactile sensor that can sense force on both planes.

A method and a system for monitoring a movement of a user according to an embodiment of the present disclosure can naturally monitor respiration or heartbeat of the user who sits on the chair by using the flexible tactile sensor.

A method and a system for monitoring a movement of a user according to an embodiment of the present disclosure can sense whether the user who sits on the chair dozes by using the flexible tactile sensor and call attention of the user.

A method and a system for monitoring a movement of a user according to an embodiment of the present disclosure can correct a seating posture of the user by using the flexible tactile sensor.

DESCRIPTION OF EMBODIMENTS

Figure 1:
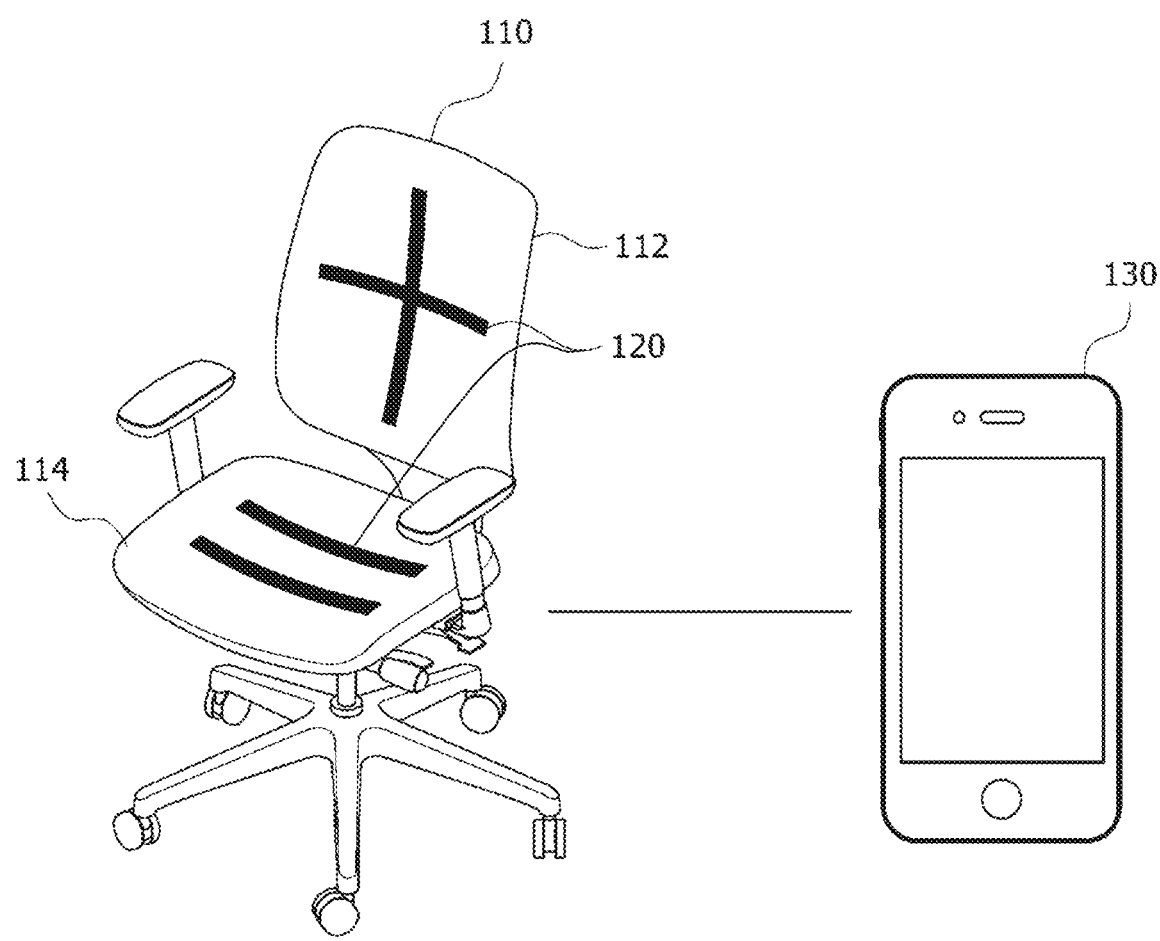
FIG. 1 is a diagram for describing a user state monitoring system according to an embodiment of the present disclosure.

The scope of the present disclosure is not limited to the disclosed embodiments. That is, since embodiments of the invention can be variously changed and have various forms, the scope of the present disclosure should be understood to include equivalents capable of realizing the technical spirit. Further, it should be understood that since a specific embodiment should include all objects or effects or include only the effect, the scope of the present disclosure is limited by the object or effect.

Meanwhile, meanings of terms described in the present application should be understood as follows.

The terms "first," "second,", and the like are used to differentiate a certain component from other components, but the scope of should not be construed to be limited by the terms. For example, a first component may be referred to as a second component, and similarly, the second component may be referred to as the first component.

It should be understood that, when it is described that a component is "connected to" another component, the component may be directly connected to another component or a third component may be present therebetween. In contrast, it should be understood that, when it is described that an element is "directly connected to" another element, it is understood that no element is present between the element and another element. Meanwhile, other expressions describing the relationship of the components, that is, expressions such as "between" and "directly between" or "adjacent to" and "directly adjacent to" should be similarly interpreted.

It is to be understood that the singular expression encompass a plurality of expressions unless the context clearly dictates otherwise and it should be understood that term "include" or "have" indicates that a feature, a number, a step, an operation, a component, a part or the combination thereof described in the specification is present, but does not exclude a possibility of presence or addition of one or more other features, numbers, steps, operations, components, parts or combinations thereof, in advance.

In each step, reference numerals (e.g., a, b, c, etc.) are used for convenience of description, the reference numerals are not used to describe the order of the steps and unless otherwise stated, it may occur differently from the order specified. That is, the respective steps may be performed similarly to the specified order, performed substantially simultaneously, and performed in an opposite order.

The present disclosure can be implemented as a computer-readable code on a computer-readable recording medium and the computer-readable recording medium includes all types of recording devices for storing data that can be read by a computer system. Examples of the computer readable recording medium include a ROM, a RAM, a CD-ROM, a magnetic tape, a floppy disk, an optical data storage device, and the like and further include a device implemented as a type of a carrier wave (e.g., transmission through the Internet). Further, the computer readable recording media may be stored and executed as codes which may be distributed in the computer system connected through a network and read by a computer in a distribution method.

If it is not contrarily defined, all terms used herein have the same meanings as those generally understood by those skilled in the art. Terms which are defined in a generally used dictionary are interpreted to have the same meaning as the meaning in the context of the related art, and are not interpreted as an ideal meaning or excessively formal meanings unless clearly defined in the present application.

FIG. 1 is a diagram for describing a user state monitoring system according to an embodiment of the present disclosure.

Referring to FIG. 1, the user state monitoring system 100 includes a chair 110, a flexible tactile sensor 120, and a monitoring apparatus 130.

The chair 110 comprises a backrest 112 and a seat plate 114 and a user may sit on the chair 110. The chair 110 includes all chairs of a type which the user may sit on. For example, the chair 110 includes all chairs embedded in furniture such as a household chair or an office chair, a vehicle such as a car, an airplane, or the like. At least one flexible tactile sensor 120 may be positioned in or on the chair 110 in order to sense a motion of the user.

The flexible tactile sensor 120 may be positioned on the backrest 112 or the seat plate 114 of the chair 110 and sense the motion of the user who sits on the corresponding chair 110 and transmits sensed values according to the motion to the outside. For example, the flexible tactile sensor 120 may sense movement of the user who sits on the chair 110 or the motion of a part of (e.g., muscle, tissue, etc.) of a body of the user. The flexible tactile sensor 120 senses force on both planes to accurately sense the motion of the user.

In an embodiment, the flexible tactile sensor 120 may include a detachment/attachment portion on one plane and may be detached from/attached to the chair through the detachment/attachment portion. In another embodiment, the flexible tactile sensor 120 may be embedded in the chair 110. In another embodiment, the flexible tactile sensor 120 may be embedded in a pad, a mat, or a cushion and the pad, the mat or the cushion in which the flexible tactile sensor 120 is embedded may be detached from/attached to a frame of the chair. Hereinafter, for easy description, the user state monitoring system 100 will be described based on an embodiment where the flexible tactile sensor 120 is embedded in the chair 110.

Locations and the number of flexible tactile sensors 120 may be determined in consideration of requirements including a physical condition of the user, a type of state information to be sensed, and the like and the locations and the number may vary according to the requirements.

For example, in FIG. 1, a first flexible tactile sensor may be positioned vertically at a location of the backrest 112 corresponding to the spine in the backrest 112 of the chair 110 and a second flexible tactile sensor may be positioned horizontally at a location corresponding to a chest. Further, a third flexible tactile sensor may be positioned horizontally at a location corresponding to a hip portion and a fourth flexible tactile sensor may be positioned horizontally at a location corresponding to a thigh.

The monitoring apparatus 130 monitors the state of the user who sits on the chair 110 based on the sensed value received from at least one flexible tactile sensor. In one embodiment, the monitoring apparatus 130 may measure respiration or heartbeat of the user based on the sensed value received from the flexible tactile sensor at a location corresponding to a specific portion of the user. In an embodiment, the monitoring apparatus 130 may calculate an amount or a distribution of force applied to at least one flexible tactile sensor based on the received sensing value and monitor whether the user dozes or a seating posture of the user based on a pattern of the calculated amount or distribution of the force.

In an embodiment, the monitoring apparatus 130 may include a mobile terminal, a smart phone, a tablet PC, a wearable PC, or a laptop PC. In another embodiment, the monitoring apparatus 130 may include a vehicle information system or an auxiliary device embedded in or connected with the chair.

The monitoring apparatus 130 may be connected with at least one flexible tactile sensor 120 by using a wireless communication means or a wired communication means such as short-range wireless communication.

Figure 2:
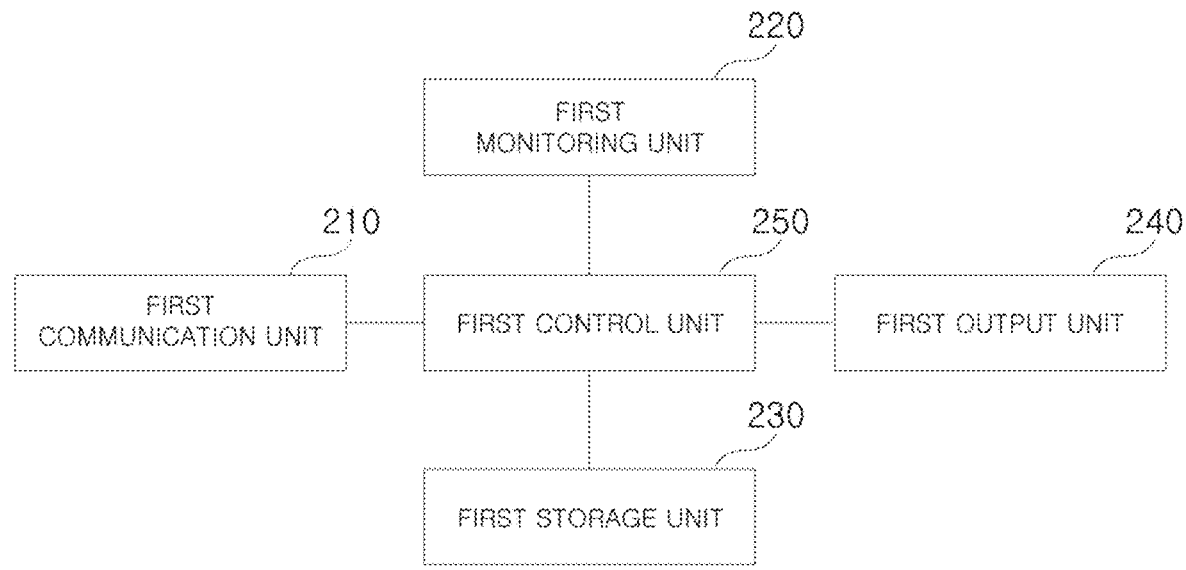
FIG. 2 is a block diagram illustrating a configuration of a monitoring apparatus illustrated in FIG. 1.

FIG. 2 is a block diagram illustrating an example configuration of the monitoring apparatus illustrated in FIG. 1.

Referring to FIG. 2, the monitoring apparatus 130 includes a first communication unit 210, a first monitoring unit 220, a first storage unit 230, a first output unit 240, and a first control unit 250. The first communication unit 210 receives the sensed value from at least one flexible tactile sensor 120 positioned in the chair 110. For example, the first communication unit 210 may correspond to a Bluetooth module, a short-range wireless communication module, or a wired communication module.

The first monitoring unit 220 monitors the state of the user based on the received sensed value. In an embodiment, the first monitoring unit 220 may measure and monitor the respiration or heartbeat of the user based on the sensed value received from the flexible tactile sensor 120 at the location corresponding to the specific portion of the user. For example, the first monitoring unit 220 may measure and monitor the respiration or heartbeat of the user based on the sensed value received from the flexible tactile sensor 120 at the location corresponding to a femoral artery of the user.

In an embodiment, the first monitoring unit 220 may calculate the amount or the distribution of the force applied to at least one flexible tactile sensor 120 based on the received sensing value and monitor whether the user dozes based on the pattern of the calculated amount or distribution of the force.

For example, when it is analyzed that a weight of the user is shifted forward in a short time (a predetermined time) based on the sensed value received from the flexible tactile sensor 120 positioned on the seat plate, the first monitoring unit 220 determines that the user dozes. Alternatively, when the motion of the user is not sensed for a predetermined time (a preset time) or more, the first monitoring unit 220 may determine that the user dozes.

In an embodiment, the first monitoring unit 220 may calculate the amount or the distribution of the force applied to at least one flexible tactile sensor 120 based on the received sensing value and monitor the posture or the user based on the pattern of the calculated amount or distribution of the force.

For example, the first monitoring unit 220 may compare the posture of the user and a predetermined posture based on the pattern of the calculated amount or distribution of the force and guide the user to take a correct posture. For example, the first monitoring unit 220 may compare the pattern of the amount or distribution of the force calculated based on the received sensed value and the pattern of the amount or distribution of the force of a predetermined correct posture. The first monitoring unit 220 may determine that the user sits in an incorrect posture when a difference between both patterns is equal to or more than a predetermined ratio.

The first monitoring unit 220 may be implemented as a software module or a hardware module, or a combination of the software and hardware modules.

The first storage unit 230 stores data necessary for driving and operating the monitoring apparatus 130. For example, the first storage unit 230 may store an operating program, a monitoring application, the received sensed value, or monitoring result data of the monitoring apparatus 130. The first storage unit 230 may be implemented as a volatile or non-volatile memory.

The first output unit 240 outputs the state of the monitoring apparatus, a monitoring result, and the like. For example, the first output unit 240 may correspond to a speaker or a display.

The first control unit 250 controls the first communication unit 210, the first monitoring unit 220, the first storage unit 230, and the first output unit 240 to receive the sensed value and control user state monitoring and an output of the monitoring result based on the received value.

For example, the first control unit 250 may control the first output unit 240 to output the measured respiration or heartbeat of the user. Alternatively, when the first control unit 250 determines that the user dozes, the first control unit 250 may control the first output unit 240 to output an alarm, thereby calling the attention of the user. Alternatively, when the first control unit 250 determines that the seating posture of the user is not the correct posture, the first control unit 250 may control the first output unit 240 to output a guide message, thereby guiding the user to sit in the correct posture.

In an embodiment, the first control unit 250 may transmit the monitoring result to the outside or may control a peripheral device based on the monitoring result.

For example, the first control unit 250 may transmit the measured respiration or heartbeat of the user to a medical person's terminal or a medial institution. The measured respiration or heartbeat of the user can be transmitted to a predetermined medical person's terminal or medial institution through a cellular communication network or a wireless LAN.

Alternatively, when the first control unit 250 determines that the user dozes, the first control unit 250 transmits a control signal for controlling an operation of the peripheral device to the corresponding peripheral device to call the attention of the user. For example, the first control unit 250 transmits the control signal to a vibration device provided on the backrest 112 or the seat plate 114 of the chair 110 to vibrate the vibration device.

Figure 3:
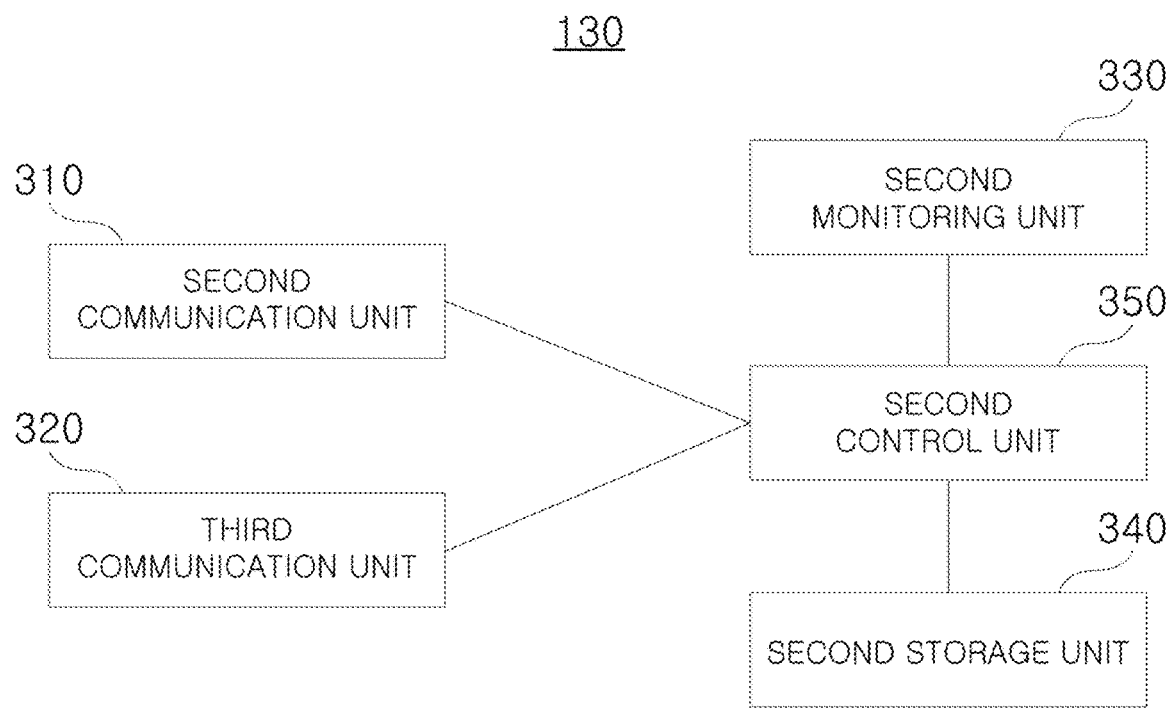
FIG. 3 is a block diagram illustrating another configuration of the monitoring apparatus illustrated in FIG. 1.

FIG. 3 is a block diagram illustrating another example configuration of the monitoring apparatus illustrated in FIG. 1.

Referring to FIG. 3, the monitoring apparatus 130 includes a second communication unit 310, a third communication unit 320, a second monitoring unit 330, a second storage unit 340, and a second control unit 350.

FIG. 3 illustrates an example of the monitoring apparatus 130 associated with another system. For example, the chair 110 may correspond to the (driver) seat in the vehicle and the monitoring apparatus 130 may be associated with a vehicle information system controlling the device in the vehicle. Hereinafter, a configuration different from FIG. 2 will be primarily described for clarity and conciseness.

The second communication unit 310 receives the sensed value from at least one flexible tactile sensor 120 positioned in the chair 110. For example, the second communication unit 310 may correspond to the Bluetooth module, the short-range wireless communication module, or the wired communication module.

The third communication unit 320 transmits/receives data to/from the vehicle information system. For example, the third communication unit 320 may transmit/receive the data to/from the vehicle information system via a control area network (CAN) network.

The second monitoring unit 330 may monitor the respiration of the user, the heartbeat of the user, whether the user dozes, or the posture of the user based on the sensed value received from the flexible tactile sensor.

In an embodiment, the second monitoring unit 330 may monitor whether the user dozes or the posture of the user by compensating the sensed value based on an impact value measured by an impact sensor of the vehicle. For example, the vehicle information system may receive an impact value measured from the impact sensor provided, for example, in a suspension of the vehicle, or the like and transmit the received impact value to the monitoring apparatus 130. The monitoring apparatus 130 receives the impact value through the third communication unit 320 and compensates the sensed value received from the flexible tactile sensor based on the received impact value to monitor whether the user dozes or the posture of the user.

For example, the second monitoring unit 330 may calculate the amount of force or the distribution of the force by compensating the force applied by a body of the user to the chair according to the impact value. In an embodiment, the second monitoring unit 330 may calculate a compensation value by multiplying the impact value by a compensation coefficient according to the impact value. The compensation coefficient may be calculated in advance through experiments, or the like and stored in the monitoring apparatus 130. In an embodiment, the second monitoring unit 330 receives information on an impact direction as well as the impact value from the vehicle information system and compensates the force applied by the body of the user to the chair based on the received information to calculate the amount of the force or the distribution of the force. The compensation coefficient according to the impact direction and the impact value may be calculated in advance through the experiments, or the like and stored in the monitoring apparatus 130.

In an embodiment, when it is determined that the user (e.g., a driver) dozes, the second control unit 350 transmits the control signal for controlling the operation of the device in the vehicle to the vehicle information system to call the attention of the user. For example, the second control unit 350 may transmit a control signal for controlling an audio of the vehicle to the vehicle information system through the third communication unit 320. The vehicle information system may turn on the audio of the vehicle or adjust an audio volume based on the received control signal.

Alternatively, the second control unit 350 may transmit a control signal for controlling a control signal for controlling opening/closing of a window of the vehicle or a control signal for controlling an air-conditioning system of the vehicle to the vehicle information system. The vehicle information system opens/closes the window based on the received control signal or controls the air-conditioning system to adjust the temperature in the vehicle.

Alternatively, the second control unit 350 may transmit a control signal for controlling a horn of the vehicle to the vehicle information system. The vehicle information system rings the horn based on the received control signal to call the attention of the user.

In an embodiment, when it is determined that the user (e.g., the driver) sits in an incorrect posture, the second control unit 350 may transmit a control signal for a location or an angle of the chair to the vehicle information system. The vehicle information system may adjust the location or angle of the chair by controlling a chair adjusting apparatus based on the received control signal. The chair adjusting apparatus may allow the posture of the user to be proximate to a predetermined posture by adjusting the location or the angle of the chair.

In an embodiment, when the impact value measured by the impact sensor of the vehicle is equal to or more than a predetermined value, the second control unit 350 may not transmit the control signal to the vehicle information system. For example, when the impact value is equal to or more than a predetermined value (a value in which the sensed value may not be corrected), the second control unit 350 may not transmit the control signal to the vehicle information system for stability of the system.

Figure 4:
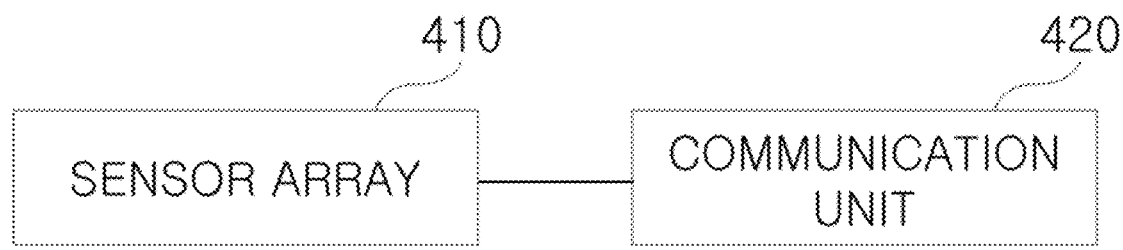
FIG. 4 is a block diagram illustrating a configuration of a flexible tactile sensor illustrated in FIG. 1.

FIG. 4 is a block diagram illustrating an example configuration of the flexible tactile sensor illustrated in FIG. 1.

Referring to FIG. 4, the flexible tactile sensor 120 includes a tactile sensor array 410 including a plurality of tactile sensor modules and a communication unit 420 transmitting a sensing value output from the tactile sensor array 410 wirelessly or by wire.

For example, the communication unit 420 may transmit the sensed value to the monitoring apparatus 130 using a wireless communication means such as Bluetooth, wireless LAN, or short-range wireless communication.

Figure 5:
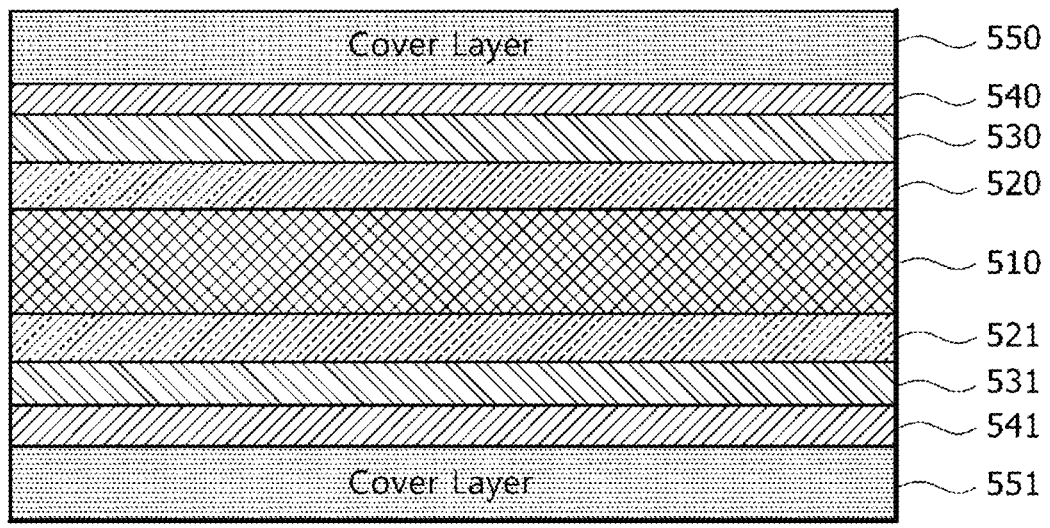
FIG. 5 is a schematic cross-sectional view of a tactile sensor module included in the flexile tactile sensor illustrated in FIG. 4.

FIG. 5 is a schematic cross-sectional view of an example tactile sensor module included in the flexile tactile sensor illustrated in FIG. 4.

Referring to FIG. 5, the flexible tactile sensor module includes a polymer layer 510, a first metal layer 520, a first sensor layer 530, a first cover layer 550, a second metal layer 521, a second sensor layer 531 and a second cover layer 551. The first metal layer 520 is formed on the top of the polymer layer 510. The first sensor layer 530 includes a strain gauge formed on the top of the first metal layer 520 and has a resistance value which varies depending on strain and a metal wire connected to the strain gauge. The first cover layer 550 protects the first sensor layer 530. The second metal layer 521 is formed on the bottom of the polymer layer 510. The second sensor layer 531 includes the strain gauge formed on the bottom of the second metal layer 521 and has the resistance value which varies depending on strain and the metal wire connected to the strain gauge. The second cover layer 551 protects the second sensor layer 531.

The polymer layer 510 may be flexibly bent by external force while maintaining a structure of a sensor. In an embodiment, the polymer layer 510 may be a polyimide (PI) layer. Polyimide has high thermal stability, stable physical and chemical properties, is thin, and has excellent flexibility. In an embodiment, the polymer layer 510 may be formed with a thickness of about 25 μm.

The first metal layer 520 and the second metal layer 521 are formed on the top (alternatively, outward) and the bottom (alternatively, outward) of the polymer layer 510, respectively. The first metal layer 520 and the second metal layer 521 may be formed by depositing nickel-chromium (Ni—Cr) on the upper and lower parts of the polymer layer 510. In an embodiment, each of the first metal layer 520 and the second metal layer 521 may be formed with a thickness of about 400 ÅA. In an embodiment, the first metal layer 520 and the second metal layer 521 may be deposited only at a location where the strain gauge is to be patterned.

The first sensor layer 530 includes the strain gauge formed above the first metal layer 520 and having the resistance value which varies depending on the strain and the metal wire connected to the strain gauge. The strain gauge may be patterned on the top of the first metal layer 520 and thereafter, the metal wire may be connected to the strain gauge. The metal wires are connected to one end and the other end of the strain gauge, respectively to be connected to the first and second electrodes. The metal wire is patterned with, for example, copper (Cu) to be connected to the strain gauge. In an embodiment, the first sensor layer 530 may be formed with a thickness of about 13 μm.

The second sensor layer 531 includes the strain gauge formed on the bottom of the second metal layer 521 and having the resistance value which varies depending on the strain and the metal wire connected to the strain gauge. A description of the second sensor layer 531 is the same as that of the first sensor layer 530.

The first cover layer 550 protecting the first sensor layer 530 may be formed on top of the first sensor layer 530 and the second cover layer 551 protecting the second sensor layer 531 may be formed on the bottom of the second sensor layer 531. In an embodiment, the cover layers 550 and 551 may be polyester (PET) layers.

A first adhesive layer 540 may be formed on the top of the first sensor layer 530 and the first cover layer 550 may be bonded to the top of the first sensor layer 530 through the first adhesive layer 540. Similarly, a second adhesive layer 541 may be formed on the bottom of the second sensor layer 531 and the second cover layer 551 may be bonded to the bottom of the second sensor layer 531 through the second adhesive layer 541. For example, the cover layers 550 and 551 may be bonded after applying an adhesive to the sensor layers 530 and 531 or attaching an adhesive film.

The flexible tactile sensor of FIG. 5 includes sensors on both surfaces to sense force on both surfaces. For example, when the flexible tactile sensor is bent in its one side by external force, bending the flexible tactile sensor may be sensed on both surfaces (bending up and bending down), thereby increasing accuracy of the sensing. Further, the flexible tactile sensor may measure normal force applied to one point of the corresponding tactile sensor.

Figure 6:
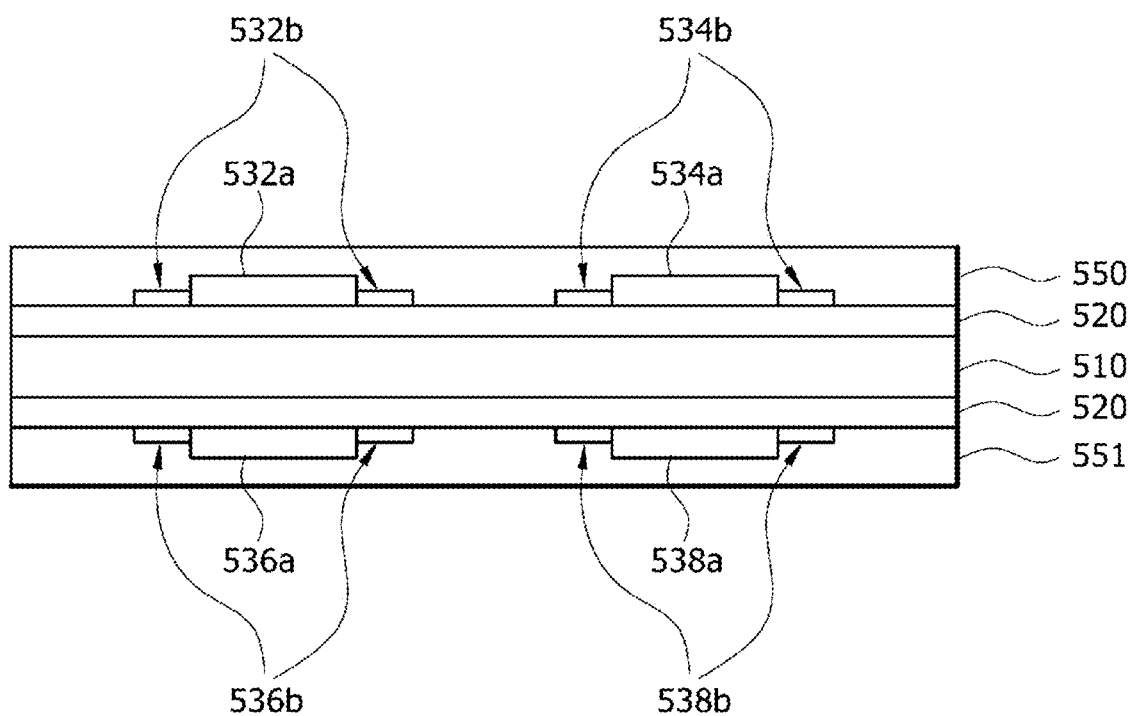
FIG. 6 is a specific cross-sectional view of the tactile sensor module illustrated in FIG. 5.

FIG. 6 is a specific cross-sectional view of the tactile sensor module illustrated in FIG. 5.

Referring to FIG. 6, the first sensor layer 530 includes a first strain gauge 532a, a first metal wire 532b connected to each of one end and the other end of the first strain gauge 532a, a second strain gauge 534a, and a second metal wire 534b connected to each of one end and the other end of the second strain gauge 534a. The first strain gauge 532a and the second strain gauge 534a may be formed to be spaced apart from each other.

In an embodiment, the first strain gauge 532a and the first metal wire 532b may correspond to driving sensor modules and the second strain gauge 534a and the second metal wire 534b may correspond to correction sensor modules. For example, the first strain gauge 532a may output a first sensing value via the first metal wire 532b and output a second sensing value for correcting the first sensing value through the second metal wire 534b.

For example, a metal strain gauge may have a resistance characteristic that resistance linearly increases as a temperature rises. Accordingly, the monitoring apparatus may include a module or an algorithm for correcting the sensed value and correct an error of the sensed value by a temperature difference between the sensor modules by using the first sensing value output from the driving sensor module and the second sensing value output from the correction sensor module.

The second sensor layer 532 includes a third strain gauge 536a, a third metal wire 536b connected to each of one end and the other end of the third strain gauge 536a, a fourth strain gauge 538a, and a fourth metal wire 538b connected to each of one end and the other end of the fourth strain gauge 538a. The third strain gauge 536a and the fourth strain gauge 538a may be formed to be spaced apart from each other.

In an embodiment, the third strain gauge 536a and the third metal wire 536b may correspond to the driving sensor modules and the fourth strain gauge 538a and the fourth metal wire 538b may correspond to the correction sensor modules. For example, the third strain gauge 536a may output a third sensing value through the first metal wire 536b and the fourth strain gauge 538a may output a fourth sensing value for correcting the third sensing value through the fourth metal wire 538b.

In an embodiment, the first metal layer and the second metal layer may be deposited over the polymer layer 510 and may be deposited only at locations 520a, 520b, 521a, and 521b where the strain gauge is patterned.

Figure 7:
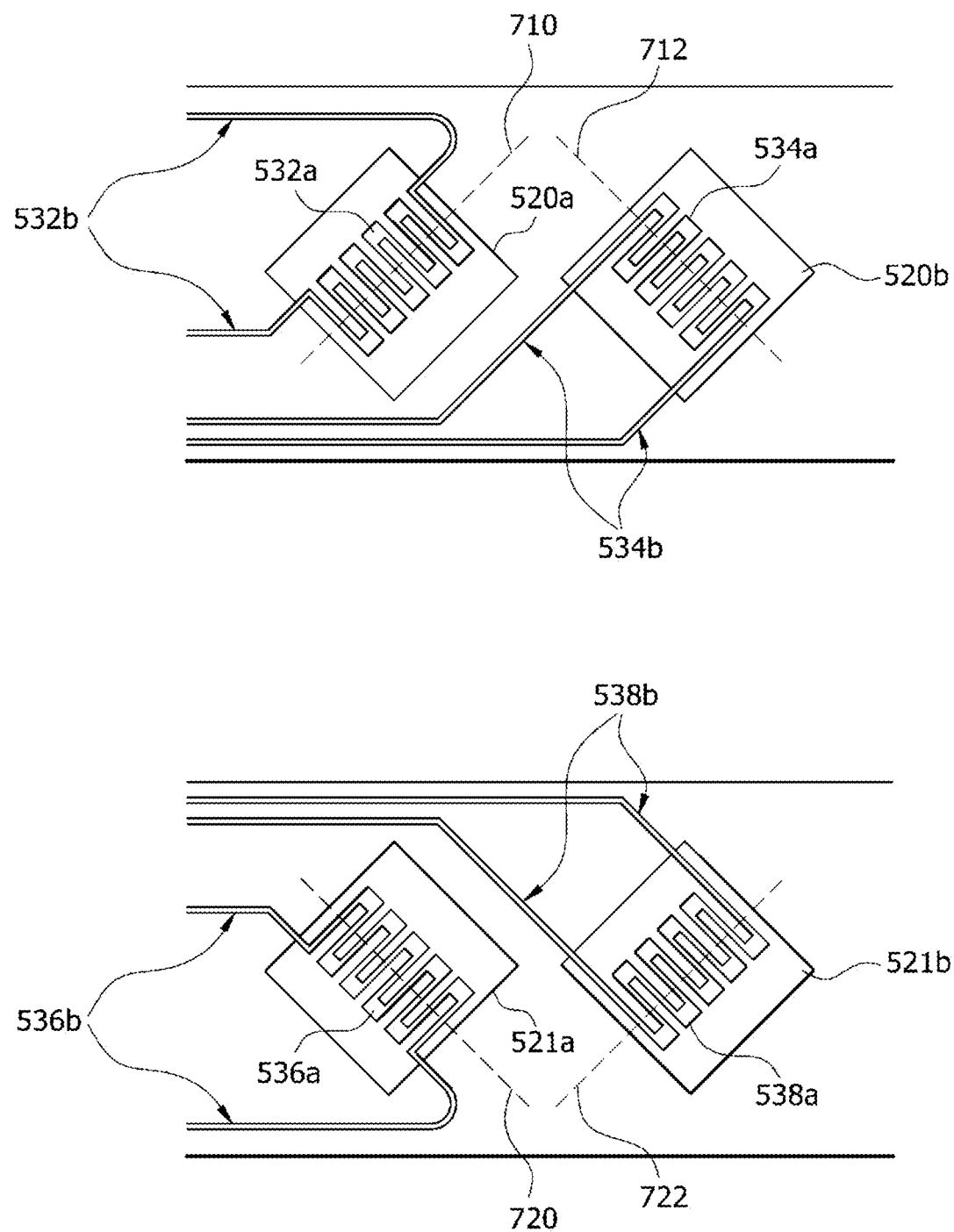
FIG. 7 is a diagram for describing a strain gauge and a metal wire of the tactile sensor module illustrated in FIG. 6.

FIG. 7 is a diagram for describing an example strain gauge and an example metal wire of the tactile sensor module illustrated in FIG. 6.

Referring to FIG. 7, the strain gauges 532a, 534a, 536a, and 538a may be patterned in a continuous 'ᄅ' shape. Each metal wire may be connected to the end of each strain gauge.

In an embodiment, lengths of line widths and lengths of gaps between lines of the strain gauges 532a and 536a of the driving sensor module and the strain gauges 534a and 538a of the correction sensor module may be different from each other. The length of the line width and the length of the gap between the lines may be implemented to be different according to an application target of the sensor or a main measurement direction of the force.

For example, the lengths of the line widths of the strain gauges 532a and 536a of the driving sensor module may be in the range of 40 μm to 90 μm, the length of the gaps between the lines may be in the range of 110 μm to 160 μm, the lengths of the line widths of the strain gauges 534a and 538a of the correction sensor module may be in the range of 50 μm to 100 μm, and the length of the gap between the lines may be in the range of 100 μm to 150 μm.

In an embodiment, the lengths of the line widths of the strain gauges 532a and 536a of the driving sensor module may be about 65 μm, the length of the gaps between the lines may be about 135 μm, the lengths of the line widths of the strain gauges 534a and 538a of the correction sensor module may be about 75 μm, and the length of the gap between the lines may be about 125 μm.

In an embodiment, the strain gauges 532a, 534a, 536a, and 538a may be formed in a direction to easily measure the bending force or the normal force. For example, the strain gauges 532a, 534a, 536a, and 538a may be formed so that an expected folding line or bending line of the flexible tactile sensor becomes horizontal to longitudinal axes 710, 712, 720, and 722 of the strain gauges 532a, 534a, 536a, and 538a. As the folding line or bending line of the flexible tactile sensor becomes horizontal to the longitudinal axes 710, 712, 720, and 722 of the strain gauges 532a, 534a, 536a, and 538a, strain rate of the strain gauge becomes larger and measurement accuracy may be thus increased. In an embodiment, the expected folding line or bending line of the flexible tactile sensor may be assumed by a designer in advance by considering an application target, an application location, or force to be measured and the strain gauges 532a, 534a, 536a, and 538a may be formed based on the assumption. For example, in FIG. 7, the first strain gauge 532a of the driving sensor module and the second strain gauge 534a of the correction sensor module may be formed such that each of the longitudinal axes 710 and 712 has a predetermined angle with a vertical axis of a plane. For example, the first strain gauge 532a and the second strain gauge 534a may be formed to be oblique to each other.

In an embodiment, the first strain gauge 532a and the second strain gauge 534a are spaced apart from each other and the respective longitudinal axes 710 and 712 cross each other to be formed to have a shape of '/\'.

The third strain gauge 536a of the driving sensor module and the fourth strain gauge 538a of the correction sensor module may be formed such that each of the longitudinal axes 720 and 722 has a predetermined angle with the vertical axis of the plane. For example, the third strain gauge 536a and the fourth strain gauge 538a may be formed to be oblique to each other.

In an embodiment, the third strain gauge 536a and the fourth strain gauge 538a are spaced apart from each other and the respective longitudinal axes 720 and 722 cross each other to be formed to have the shape of '\/'.

In an embodiment, the first strain gauge 532a and the third strain gauge 536a may be formed at opposite locations corresponding to each other and the second strain gauge 534a and the fourth strain gauge 538a may be formed at opposite locations corresponding to each other. In another embodiment, the first strain gauge 532a and the second strain gauge 534a at one side and the third strain gauge 536a and the fourth strain gauge 538a may be formed to cross each other. For example, the first strain gauge 532a, the third strain gauge 536a, the second strain gauge 534a, and the fourth strain gauge 538a may be formed to cross each other in order.

In the flexible tactile sensor configured as above, the sensors are provided on both surfaces to accurately sense the force on both surfaces.

Figure 8:
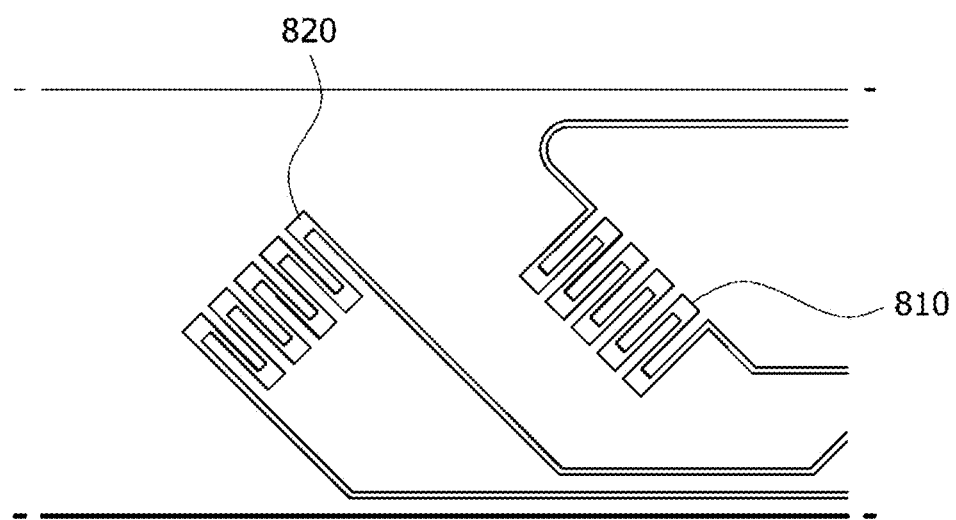
FIG. 8 is a diagram illustrating an implementation example of the tactile sensor module illustrated in FIG. 6.

FIG. 8 is a diagram illustrating an implementation example of the tactile sensor module illustrated in FIG. 6.

Referring to FIG. 8, it can be seen that a driving sensor module 810 and a correction sensor module 820 are formed on one side of the flexible tactile sensor. The strain gauges of the tactile sensor module may be formed on the same surface or on different surfaces as illustrated in FIG. 8.

FIG. 9 is a diagram illustrating another implementation example of the tactile sensor module.

Figure 9A:
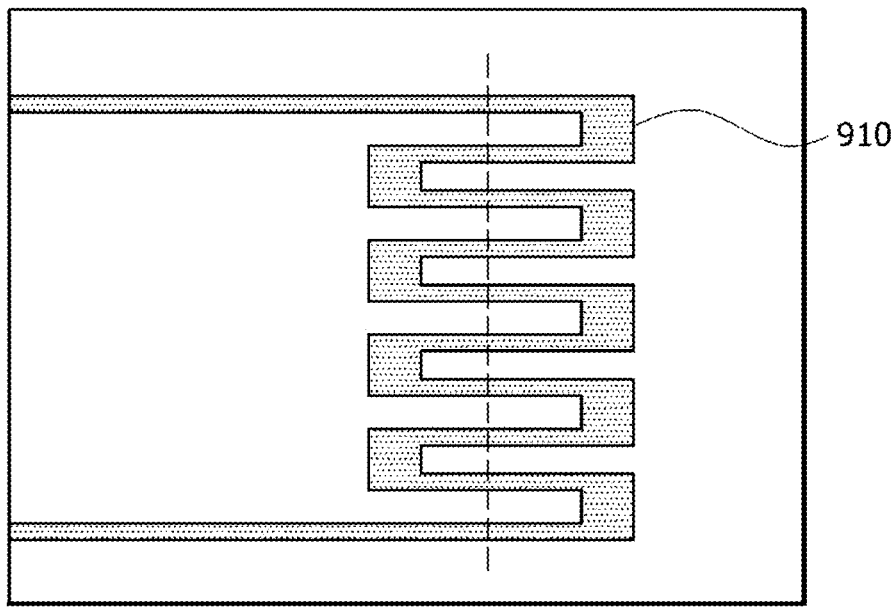
FIGS. 9A and 9B illustrate another implementation example of the tactile sensor module.
Figure 9B:
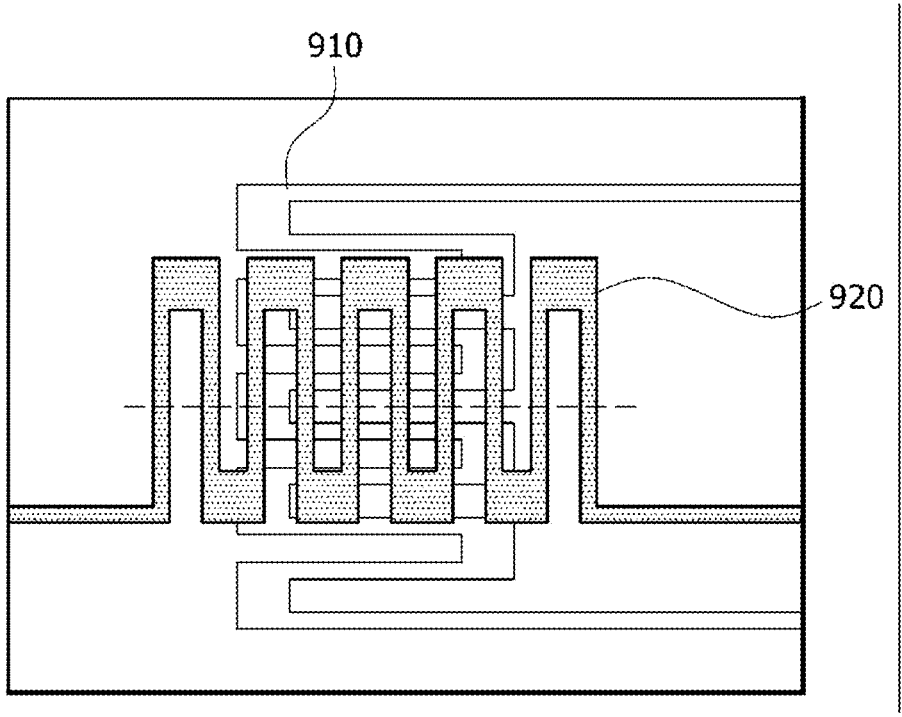

Referring to FIG. 9, a first strain gauge 910 may be formed on a first surface (FIG. 9A) and a second strain gauge 920 may be formed on a second surface (an opposite surface of the first surface) (FIG. 9B). In an embodiment, the first strain gauge 910 and the second strain gauge 920 may be formed such that the respective longitudinal axes are perpendicular to each other. In another embodiment, the first strain gauge 910 and the second strain gauge 920 may be formed such that the respective longitudinal axes are cross obliquely to each other.

For example, in FIG. 9, the first strain gauge 910 may be formed such that the longitudinal axis is perpendicular to the horizontal plane of the first surface (FIG. 9A) and the second strain gauge 920 may be formed such that the longitudinal axis is parallel to the horizontal plane of the second surface (FIG. 9B) and perpendicular to each other. Through the tactile sensor module formed as described above, a user may confirm a strain direction according to applied force.

In an embodiment, the first strain gauge 910 may correspond to the strain gauge of the first driving sensor module and the second strain gauge 920 may correspond to the strain gauge of the second driving sensor module. In this case, the monitoring server may include a module or algorithm for correcting the sensing value in a predetermined manner and may correct the sensing value output from each driving sensor module.

In another embodiment, the first strain gauge 910 may correspond to the strain gauge of the driving sensor module and the second strain gauge 920 may correspond to the strain gauge of the correction sensor module.

Figure 10:
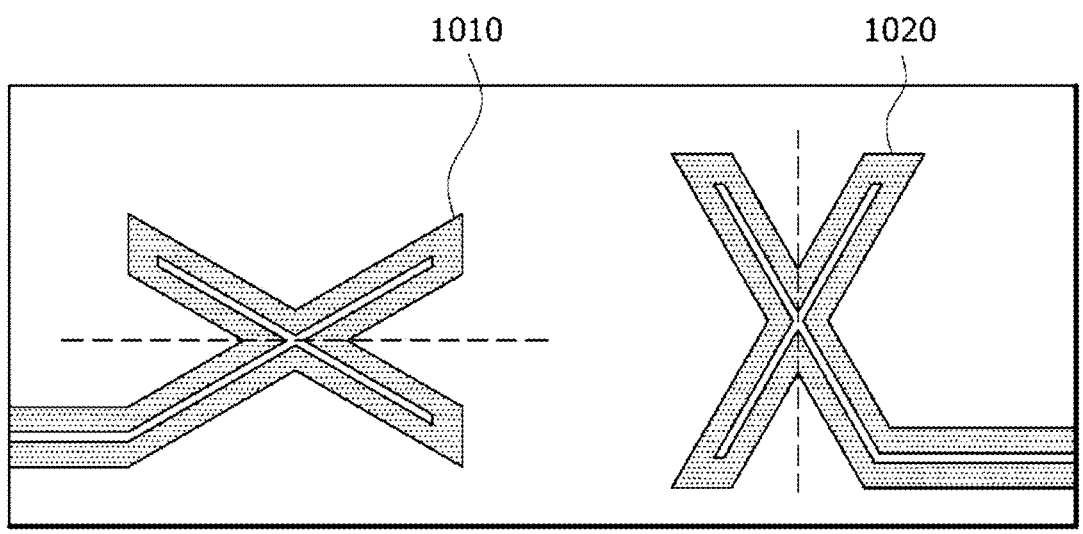
FIG. 10 is a diagram illustrating yet another implementation example of the tactile sensor module.

FIG. 10 is a diagram illustrating yet another implementation example of the tactile sensor module.

Referring to FIG. 10, a first strain gauge 1010 and a second strain gauge 1020 may be formed on the same plane. In another embodiment, the first strain gauge 1010 and the second strain gauge 1020 may be formed on different surfaces or planes.

Each of the strain gauges 1010 and 1020 may be patterned in an 'X' shape and metal wires may be connected to ends of the strain gages 1010 and 1020, respectively.

In an embodiment, the longitudinal axis of the first strain gauge 1010 and the longitudinal axis of the second strain gauge 1020 may be formed to be different directions. For example, in FIG. 10, the first strain gauge 1010 may be formed such that the longitudinal axis is parallel to the horizontal plane of the corresponding surface and the second strain gauge 1020 may be formed such that the longitudinal axis is perpendicular to the horizontal surface of the corresponding surface. In another embodiment, the longitudinal axis of the first strain gauge 1010 and the longitudinal axis of the second strain gauge 1020 may be formed to be the same direction.

In an embodiment, the first strain gauge 1010 may correspond to the strain gauge of the first driving sensor module and the second strain gauge 1020 may correspond to the strain gauge of the second driving sensor module. In this case, the monitoring server may include a module or algorithm for correcting the sensing value in a predetermined manner and may correct the sensing value output from each driving sensor module.

In another embodiment, the first strain gauge 1010 may correspond to the strain gauge of the driving sensor module and the second strain gauge 1020 may correspond to the strain gauge of the correction sensor module.

In the embodiments of FIGS. 8 to 10, each flexible tactile sensor includes strain gauges of the same pattern, but one flexible tactile sensor may include strain gauges of different patterns. For example, one flexible tactile sensor may include both a strain gauge of a continuous 'ㄹ' shape and a strain gauge having an 'X' shape.

Figure 11:
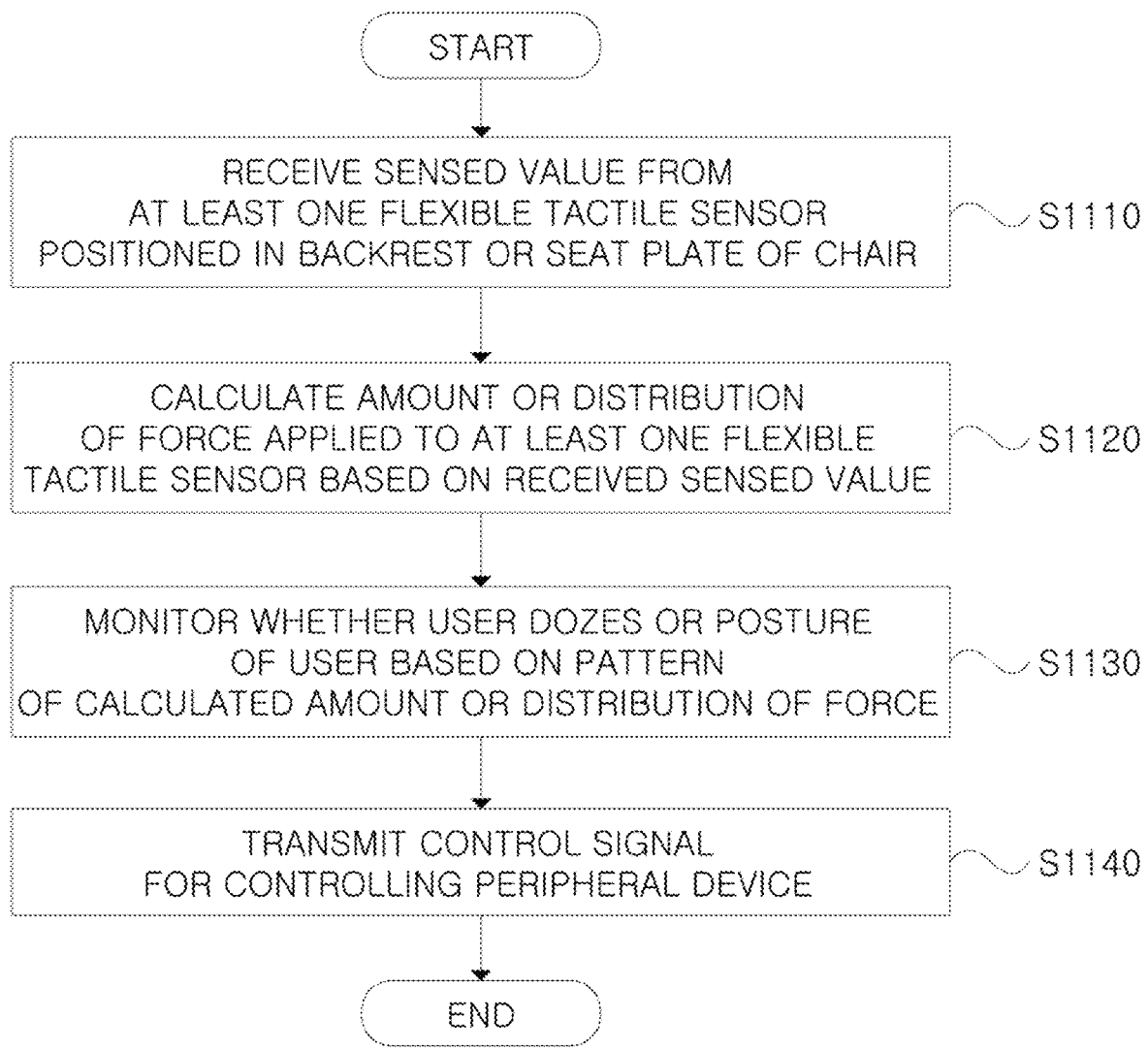
FIG. 11 is a flowchart for describing a user state monitoring method performed by a user state monitoring system illustrated in FIG. 1.

FIG. 11 is a flowchart for describing a user state monitoring method performed by the user state monitoring system illustrated in FIG. 1.

Referring to FIG. 11, the monitoring apparatus 130 receives the sensed value from at least one flexible tactile sensor 120 positioned on the backrest 112 or the seat plate 114 of the chair 110 (step S1110). The flexible tactile sensor includes a sensor array including the tactile sensor module and a communication unit. The tactile sensor module may have a structure described in FIGS. 5 to 10.

The monitoring apparatus 130 calculates the distribution or the distribution of the force applied to at least one flexible tactile sensor based on the received sensed value (step S1120).

The monitoring apparatus 130 monitors whether the user dozes or the posture of the user based on the pattern of the calculated amount or distribution of the force (step S1130).

In an embodiment, the monitoring apparatus 130 may measure the respiration or heartbeat of the user based on the sensed value received from the flexible tactile sensor at the location corresponding to the specific portion of the user.

For example, when it is analyzed that the weight of the user is shifted forward in a short time (a predetermined time) based on the sensed value received from the flexible tactile sensor positioned on the seat plate, the first monitoring apparatus 130 may determine that the user dozes. Alternatively, when the motion of the user is not sensed for a predetermined time (a preset time) or more, the monitoring apparatus 130 may determine that the user dozes.

Alternatively, the monitoring apparatus 130 compares the posture of the user and the predetermined posture based on the pattern of the calculated amount or distribution of the force and when the difference between both postures is equal to or more than a predetermined ratio, the monitoring apparatus 130 may determine that the user sits in the incorrect posture.

The monitoring apparatus 130 may transmit the control signal for controlling the peripheral device based on a result of monitoring whether the user dozes or the posture of the user (step S1140).

In an embodiment, the monitoring apparatus 130 may directly transmit the control signal to the peripheral device. For example, the monitoring apparatus 130 transmits the control signal to the vibration device provided in the backrest 112 or the seat plate 114 of the chair 110 to drive the vibration device.

In another embodiment, the monitoring apparatus 130 may transmit the control signal to an associated system. For example, the monitoring apparatus 130 may transmit the control signal for controlling the audio, the window, the horn, or the chair adjusting apparatus of the vehicle to the vehicle information system.

Logical blocks, modules or units described in connection with embodiments disclosed herein can be implemented or performed by a computing device having at least one processor, at least one memory and at least one communication interface. The elements of a method, process, or algorithm described in connection with embodiments disclosed herein can be embodied directly in hardware, in a software module executed by at least one processor, or in a combination of the two. Computer-executable instructions for implementing a method, process, or algorithm described in connection with embodiments disclosed herein can be stored in a non-transitory computer readable storage medium.

The present disclosure has been described with reference to the preferred embodiments, but those skilled in the art will understand that the present disclosure can be variously modified and changed without departing from the spirit and the scope of the present disclosure which are defined in the appended claims.

INDUSTRIAL APPLICABILITY

The present disclosure relates to a technique that can monitor a state of a user, and particularly, to a method and a system for monitoring a state of a user, which monitor a state of a user who sits on a chair by using a flexible tactile sensor and call attention of the user or correct a posture of the user.

What is claimed is:
1. A system for monitoring a state of a user, the system comprising:
 a chair comprising a backrest and a seat plate;
 at least one flexible tactile sensor positioned in at least one of the backrest and the seat plate and configured to sense a motion of the user on the chair; and
 a monitoring apparatus configured to monitor a state of the user based on a sensed value received from the at least one flexible tactile sensor,
 wherein the at least one flexible tactile sensor includes a tactile sensor array comprising a plurality of tactile sensor modules, and
 wherein each of the plurality of tactile sensor modules includes:
 polymer layer,
 a first metal layer formed over the polymer layer,
 a first sensor layer formed over the first metal layer, the first sensor layer comprising a first strain gauge configured to change resistance based on a first strain and a first metal wire connected to the first strain gauge,
 a first cover layer configured to protect the first sensor layer,
 a second metal layer formed under the polymer layer,
 a second sensor layer formed under the second metal layer, the second sensor layer comprising a second strain gauge configured to change resistance based on a second strain and a second metal wire connected to the second strain gauge, and a second cover layer configured to protect the second sensor layer.

2. The system of claim 1, wherein the at least one flexible tactile sensor is positioned at a location corresponding to a femoral artery of the user.

3. The system of claim 1, wherein the monitoring apparatus is configured to calculate an amount or a distribution of force applied to the at least one flexible tactile sensor based on the sensed value and configured to determine dozing of the user or a seating posture of the user based on a pattern of the calculated amount or distribution of the force.

4. A method for monitoring a state of a user, the method comprising:

receiving a sensed value from at least one flexible tactile sensor positioned in a backrest or a seat plate of a chair;

calculating an amount or a distribution of force applied to the at least one flexible tactile sensor based on the received sensed value; and monitoring dozing or a posture of the user based on a pattern of the calculated amount or distribution of the force, wherein the at least one flexible tactile sensor includes a tactile sensor array comprising a plurality of tactile sensor modules, and wherein each of the plurality of tactile sensor modules includes:

a polymer layer, a first metal layer formed over the polymer layer, a first sensor layer formed over the first metal layer, the first sensor layer comprising a first strain gauge configured to change resistance based on a first strain and a first metal wire connected to the first strain gauge, a first cover layer configured to protect the first sensor layer, a second metal layer formed under the polymer layer, a second sensor layer formed under the second metal layer, the second sensor layer comprising a second strain gauge configured to change resistance based on a second strain and a second metal wire connected to the second strain gauge, and a second cover layer configured to protect the second sensor layer.

5. A system for monitoring a state of a user, the system comprising:

a chair comprising a backrest and a seat plate;

at least one flexible tactile sensor positioned in at least one of the backrest and the seat plate and configured to sense pressure applied to at least one of the backrest and the seat plate; and a monitoring unit configured to monitor a state of user on the chair based on a sensed value received from the at least one flexible tactile sensor, wherein the at least one flexible tactile sensor includes a tactile sensor array comprising a plurality of tactile sensor modules, and wherein each of the plurality of tactile sensor modules includes:

a polymer layer, a first metal layer formed over the polymer layer, a first sensor layer formed over the first metal layer, the first sensor layer comprising a first strain gauge configured to change resistance based on a first strain and a first metal wire connected to the first strain gauge, a first cover layer configured to protect the first sensor layer, a second metal layer formed under the polymer layer, a second sensor layer formed under the second metal layer, the second sensor layer comprising a second strain gauge configured to change resistance based on a second strain and a second metal wire connected to the second strain gauge, and a second cover layer configured to protect the second sensor layer.

6. The system of claim 5, wherein the at least one flexible tactile sensor comprises a first set of flexible tactile sensors positioned in the backrest and a second set of flexible tactile sensors positioned in the seat plate.

7. The system of claim 6, wherein the first and second sets of flexible tactile sensors are arranged in different forms.

8. The system of claim 6, wherein the first set of flexible tactile sensors comprises a plurality of flexible tactile sensors that do not cross each other.

9. The system of claim 6, wherein the second set of flexible tactile sensors comprises a plurality of flexible tactile sensors that cross each other.

* * * * *